(12) United States Patent
Buszman et al.

(10) Patent No.: US 12,263,082 B2
(45) Date of Patent: Apr. 1, 2025

(54) LOW PROFILE BALLOON EXPANDABLE ARTIFICIAL PROSTHETIC HEART VALVE, PARTICULARLY AORTIC, FOR TRANSCATHETER IMPLANTATION

(71) Applicants: AMERICAN HEART OF POLAND S.A., Ustroń (PL); CENTRUM MATERIAŁÓW POLIMEROWYCH I WĘGLOWYCH POLSKIEJ AKADEMII NAUK, Zabrze (PL); POLITECHNIKA ŚLĄSKA WYDZIAŁ MECHANICZNY TECHNOLOGICZNY, Gliwice (PL); ŚLĄSKIE CENTRUM CHORÓB SERCA W ZABRZU, Zabrze (PL); ZAKŁAD DOŚWIADCZALNY INSTYTUTU ZOOTECHNIKI PIB GRODZIEC ŚLĄSKI SP. Z O.O., Grodziec (PL); INNOVATIONS FOR HEART AND VESSELS SP. Z O.O., Tychy (PL); HEART TEAM SP. Z O.O., Warsaw (PL)

(72) Inventors: Pawel Buszman, Katowice (PL); Piotr Dobrzynski, Zabrze (PL); Janusz Kasperczyk, Katowice (PL); Michal Sobota, Czestochowa (PL); Katarzyna Jelonek, Czestochowa (PL); Jakub Wlodarczyk, Poronin (PL); Mateusz Stojko, Laziska Gorne (PL); Mariusz Pawlak, Zabrze (PL); Wojciech Klein, Knurow (PL); Jacek Gnilka, Gliwice (PL); Arkadiusz Mezyk, Gliwice (PL); Marian Zembala, Tarnowskie Gory (PL); Michal Zembala, Zbroslawice (PL); Joanna Sliwka, Zabrze (PL); Krzysztof Milewski, Katowice (PL); Piotr Buszman, Katowice (PL); Piotr Hirnle, Warsaw (PL); Jerzy Nozynski, Zabrze (PL)

(73) Assignee: Innovations for Heart and Vessels Sp. z o.o., Katowice (PL)

(*) Notice: Subject to any disclaimer, the term of this patent is extended or adjusted under 35 U.S.C. 154(b) by 0 days.

(21) Appl. No.: 17/262,478

(22) PCT Filed: Jul. 26, 2018

(86) PCT No.: PCT/PL2018/050038
§ 371 (c)(1),
(2) Date: Jan. 22, 2021

(87) PCT Pub. No.: WO2020/022914
PCT Pub. Date: Jan. 30, 2020

(65) Prior Publication Data
US 2021/0290382 A1 Sep. 23, 2021

(30) Foreign Application Priority Data
Jul. 24, 2018 (PL) .......................... 426432

(51) Int. Cl.
*A61F 2/24* (2006.01)
*A61F 2/82* (2013.01)
*A61F 2/95* (2013.01)

(52) U.S. Cl.
CPC .......... *A61F 2/2418* (2013.01); *A61F 2/2433* (2013.01); *A61F 2220/0033* (2013.01); *A61F 2220/0075* (2013.01)

(58) Field of Classification Search
None
See application file for complete search history.

(56) References Cited

U.S. PATENT DOCUMENTS

| 4,218,782 A | 8/1980 | Rygg |
| 5,549,635 A | 8/1996 | Solar |

(Continued)

FOREIGN PATENT DOCUMENTS

| EP | 1637176 B1 | 6/2016 |
| EP | 3332740 A1 | 6/2018 |

(Continued)

OTHER PUBLICATIONS

Mateusz Kachel et al., State-of-the-art of Transcatheter Treatment of Aortic Valve Stenosis and the Overview of the InFlow Project Aiming at Developing the first Polish TAVI System, Cardiology Journal 2017, pp. 685-694, vol. 24, No. 6. Published Dec. 29, 2017 in Poland.

(Continued)

*Primary Examiner* — Ann Schillinger
(74) *Attorney, Agent, or Firm* — Cherskov, Flaynik & Gurda, LLC

(57) ABSTRACT

A low profile balloon expandable artificial prosthetic heart valve, particularly aortic, for transcatheter implantation (Continued)

comprises a valve frame of cylindrical structure. The cuff made of the polymer material is inseparably integrated with the frame so that the valve frame in the supporting section is embedded or sewn into and covered from the internal side and from the outside with the cuff material, which folded into the interior section of the frame and in the frame valve section is formed into valve leaflets in bicuspid or tricuspid configuration and in the said section it is attached to the frame and to the frame posts, and the cuff material excess is led into the longitudinal openings in the posts. In the variant of mounting the cuff made of the polymer (artificial) material is attached to the frame in the supporting section from the outside and the cuff material is folded into the interior of the frame, and in the frame valve section it creates leaflets and commissures of the valve in bicuspid or tricuspid configuration and in this section it is attached to the frame and to the posts by sewing, and the excess of the cuff material is led into the longitudinal openings in the posts.

18 Claims, 5 Drawing Sheets

(56) References Cited

U.S. PATENT DOCUMENTS

| | | | |
|---|---|---|---|
| 6,007,543 A | 12/1999 | Ellis et al. | |
| 9,486,306 B2 * | 11/2016 | Tegels | A61F 2/2418 |
| 9,549,815 B2 * | 1/2017 | Braido | A61F 2/2433 |
| 9,775,704 B2 * | 10/2017 | Bergheim | A61L 27/50 |
| 10,232,564 B2 * | 3/2019 | Pelled | B29C 66/53245 |
| 11,013,600 B2 * | 5/2021 | Schwartz | A61F 2/2433 |
| 11,123,182 B2 * | 9/2021 | Spenser | A61F 2/2418 |
| 11,166,810 B2 * | 11/2021 | Spenser | A61F 2/2412 |
| 12,059,344 B2 * | 8/2024 | Arcaro | A61F 2/2418 |
| 2003/0114913 A1 * | 6/2003 | Spenser | A61F 2/2427 623/2.14 |
| 2003/0153974 A1 * | 8/2003 | Spenser | A61F 2/9524 623/2.14 |
| 2004/0049266 A1 | 3/2004 | Anduiza et al. | |
| 2005/0075725 A1 * | 4/2005 | Rowe | A61F 2/2418 623/2.14 |
| 2006/0025857 A1 * | 2/2006 | Bergheim | A61L 27/50 623/2.18 |
| 2010/0185277 A1 * | 7/2010 | Braido | A61F 2/2409 623/2.37 |
| 2012/0123529 A1 * | 5/2012 | Levi | A61F 2/2412 623/2.11 |
| 2012/0296418 A1 * | 11/2012 | Bonyuet | A61F 2/2415 623/2.18 |
| 2013/0131790 A1 | 5/2013 | Schreck | |
| 2014/0031924 A1 | 1/2014 | Bruchman et al. | |
| 2014/0236289 A1 | 8/2014 | Alkhatib | |
| 2016/0317305 A1 * | 11/2016 | Pelled | B29C 66/53245 |
| 2018/0206982 A1 * | 7/2018 | Haivatov | A61F 2/2412 |
| 2020/0000579 A1 * | 1/2020 | Manash | A61F 2/2418 |

FOREIGN PATENT DOCUMENTS

| | | | | |
|---|---|---|---|---|
| EP | 3705090 A1 * | 9/2020 | | A61F 2/2409 |
| WO | WO2008035337 A2 | 3/2008 | | |
| WO | WO2012048035 A2 | 4/2012 | | |

OTHER PUBLICATIONS

Visegrad Patent Institute, International Search Report for Application PCT/PL2018/050038, dated Mar. 22, 2019.
Saskia Julich, European Search Report in Application EP 18 92 7966, completed on Mar. 30, 2022.

* cited by examiner

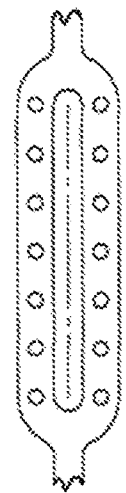   
FIG. 5A　　FIG. 5B　　FIG. 5C　　FIG. 5D
 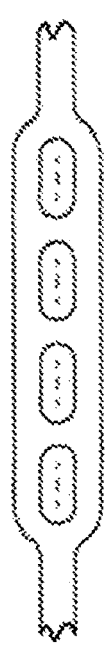
FIG. 5E　　FIG. 5F

LOW PROFILE BALLOON EXPANDABLE ARTIFICIAL PROSTHETIC HEART VALVE, PARTICULARLY AORTIC, FOR TRANSCATHETER IMPLANTATION

CROSS-REFERENCE TO RELATED APPLICATIONS

The instant application is a nationalization of PCT/PL2018/050038 with a filing date of Jul. 26, 2018, presently expired, which in turn claimed priority to Polish Patent application P.426432, filed on Jul. 24, 2018.

BACKGROUND OF THE INVENTION

The present invention relates to a low profile, balloon expandable artificial prosthetic aortic valve for transcatheter implantation. The invention relates to medical devices and developments used in treatment of heart valve defects.

SUMMARY OF THE INVENTION

Use of this type of device involves its implantation by minimally invasive transcatheter method in the place of a native valve which is impaired due to a congenital or acquired defect. Implantation is carried out under fluoroscopy by means of a low profile delivery system. This procedure is a recommended method of treating valvular disfunctions in a chosen group of patients with left arterial outflow tract stenosis, allowing to restore its functionality.

Aortic stenosis (AS) which is left arterial outflow tract obstruction is nowadays the most frequently occurring valve defect posing a serious clinical challenge for doctors. The reason is the growing number of elderly patients who cannot undergo a standard cardiac surgery due to surgical risks. It is estimated that with age the prevalence of aortic stenosis rises from 0.7% in patients 18-44 years old up to 13.3% in patients after >75 years old (publications: Nkomo V. T., Gardin J. M., Skelton T. N., et al., Burden of valvular heart disease: a population-based study. Lancet, 2006. 368(9540): p. 1005-11 DOI: 10.1016/S0140-6736(06)69208-8). European Society of Cardiology (ESC) in the recommendations from 2012 estimates that 2-7% Europeans and Americans over 65 years of age suffer from this condition. (Joint Task Force on the Management of Valvular Heart Disease of the European Society of C., European Association for Cardio-Thoracic Surgery, Vahanian A., et al., Guidelines on the management of valvular heart disease (version 2012). Eur Heart J, 2012. 33(19): p. 2451-96 DOI: 10.1093/eurheartj/ehs 109).

In the event that concomitant symptoms appear with impaired blood flow surgical treatment is indispensable, since without it the prognosis worsens significantly. Currently the basic method of treatment (gold standard) is the surgical aortic valve replacement (SAVR) which comprises implantation of a biological or mechanical prosthesis. However, this procedure affects major organs, especially in case of elderly patients (>70 years of age) among whom perioperational mortality rises with age from 1-3% to 4-8%, which is quoted in Guidelines on the management of valvular heart disease. It translates into a high percentage of patients disqualified from surgical treatment (⅓ of patients>75 years of age). It particularly refers to patients with concomitant afflictions of other organs and with high surgical risk (Euroscore 2>10%)(lung B., Cachier A., Baron G., et al., Decision-making in elderly patients with severe aortic stenosis: Why are so many denied surgery? Eur Heart J, 2005. 26(24): p. 2714-20 DOI:10.1093/eurheart/ehi471).

The alternative for such patients is a minimally-invasive method introduced into clinical setting in 2002, so-called Transcatheter Aortic Valve Replacement (TAVR). The efficacy of this method compared to conventional (surgical) method has been confirmed by the outcomes of numerous completed and ongoing trials in both high risk and lower risk patients (publication sr Mack M. J., Leon M. B., Smith C. R., et al. 5-year outcomes of transcatheter aortic valve replacement or surgical aortic valve replacement for high surgical risk patients with aortic stenosis (PARTNER 1): a randomized controlled trial. The Lancet, 2015. 385(9986): p. 2477-2484 DOI:10.1016/s0140-6736(15)60308-7.; Deeb G. M., Reardon M. J., Chetcuti S., et al., 3-Year Outcomes in High-Risk Patients Who Underwent Surgical or Transcatheter Aortic Valve Replacement. J Am Coll Cardiol, 2016.67 (22): p. 2565-74 DOI: 10.1016/j.jacc.2016.03.506; Leon M. B., Smith C. R., Mack M. J., et al., Transcatheter or Surgical Aortic-Valve Replacement in Intermediate-Risk Patients. N Engl J Med, 2016. 374(17): p. 1609-20 DOI: 10.1056/NEJMoal514616; Sondergaard L, Steinbruchel D. A., Ihlemann N., et al., Two-Year Outcomes in Patients With Severe Aortic Valve Stenosis Randomized to Transcatheter Versus Surgical Aortic Valve Replacement: The All-Comers Nordic Aortic Valve Intervention Randomized Clinical Trial. Circ Cardiovasc Interv, 2016. 9(6) DOI: 10.1161/CIRCINTERVENTIONS. 115.003665)-7)

Despite undisputed benefits, TAVR is not free from significant constraints. Relatively frequently occurring vascular injuries (4-13%) are caused mainly by large delivery systems, which although much smaller than the ones used originally (average drop from 24 F to 18 F), still need miniaturization (da Gama Ribeiro V., Vouga L., Markowitz A., et al., Vascular access in transcatheter aortic valve implantation. Int J Cardiovasc Imaging, 2011.27(8): p. 1235-43 DOI: 10.1007/s10554-011-9900-8; Cribier A., The Odyssey of TAVR from Concept to Clinical Reality. Tex Heart Inst J, 2014. 41(2) DOI: 10.14503/TH IJ-14-4137; Halapas A., Chrissoheris M., Bouboulis N., et al., Update on current TAVI 3 technology, indications, screening, and outcomes. Continuing Cardiology Education, 2016.2(1): p. 37-46 DOI: 10.1002/cce2.20). Another essential issue is the higher frequency of paravalvular leakage (PVL) occurring in patients after TVR procedure in comparison to patients after a classical surgical procedure.

The complex valve anatomy and imperfect expandable systems cause the risk of uneven opening of the prosthetic heart valve as well as its impaired apposition to the native annulus and bulb. Connected with the above mentioned issue inability to subsequent implantation of a prosthesis and its movement in case of mispositioning poses a serious challenge for scientists and constructors. These problems are addressed in detail in the publication Mollmann H., Kim W. K., Kempfert J., et al., Complications of transcatheter aortic valve implantation (TAVI): how to avoid and treat them. Heart, 2015. 101(11): p. 900-8 DOI: 10.1136/heartjnl-2013-304708. Applying biological materials for fabricating currently used TAVI prostheses rises the problem of durability. The implant like any other tissue degenerates with time and is subject to processes such as calcification or vegetation. It is essential to find methods which can improve durability and immunity of currently used materials preserving their flexibility and biocompatibility. There is another significant aspect influencing spreading of TAVR method in the world that should be noted, namely its price. Wealthy countries such as Germany and Switzerland are able to cover costs of only 34.5% and 36.2% of the demand for the therapy respectively while the European average is around 17.9%. The ideal prosthetic heart valve should be made of durable materials resistant to degradation, with biophysical properties to the greatest extent similar to native leaflets.

The prosthetic heart valve known from the patent description US2003153974 comprises a supporting frame equipped with a number of rigid carrying posts of fixed length. The said posts comprise the elements for mounting the valve leaflets with use of the suture, the bars fitted between the interlaced material forming the leaflets and the valve frame or other mounting materials. However, such construction does not allow regulation of affective stringing of the material forming the valve leaflets, and as a result it does not allow proper valve activity as well as avoidance of improper enclosure because of hindered possibility to adjust the leaflet length. The compensation of these limitations during the production process is hindered and time-consuming and it requires applying appropriate highly specialized sewing technique.

The prosthetic heart valve known from the patent description US2004049266 comprises a collapsible frame formed by a plurality of crossover posts. The consecutive post is attached to the end of each post and thereby the structure constituting the scaffold of the prosthesis is made. The exact prosthesis is made of a flexible material forming three valve leaflets, attached to the frame by means of movable rings, located in the places of crossing of individual posts. The system of mounting of such design enables proper and even apportionment of forces acting on the leaflet material. However, lack of the area where the mounting points imitating commissures are concentrated prevents proper modeling of the material and forming the hemodynamically proper structure resembling a native valve.

The prosthetic heart valve known from the patent description US2013121790 comprises a frame consisting of an extensible, cylindrical base and three commissure masts which are located at a constant distance of 120 degrees each. The exact valve is made by a cuff which consists of a material section and the exact prosthesis. The exact section preferably pericardium tissue is sewn into the commissure masts thereby forming the valve leaflets. The material section is sewn into the cylindrical base. As a result the structure resembling the native valve in form and function is achieved. There is a certain constraint about this method though. Sewing delicate pericardium tissue to the prosthesis frame involving making holes in the material may weaken its structure, which in turn carries the risk of tearing the material and of the prosthesis faster degeneration. As a consequence leakages around the valve may occur and the places of degeneration of the valve may appear. Furthermore, the shape of the stent and the manner of forming the valve may hinder the access to coronary arteries and impair the coronary flow. Additionally, such a complicated structure of the prosthesis requiring connecting a lot of elements (separate leaflets, sealing cuff and frame) prolongs the time of device manufacturing and in turn may influence the cost of manufacturing.

BRIEF DESCRIPTION OF DRAWINGS

Embodiments disclosed herein will be more fully understood from the following detailed description taken in connection with the accompanying drawings, in which:

FIG. 5 shows the views of the exemplary variants of the posts.

DETAILED DESCRIPTION OF THE INVENTION

Figure 1:
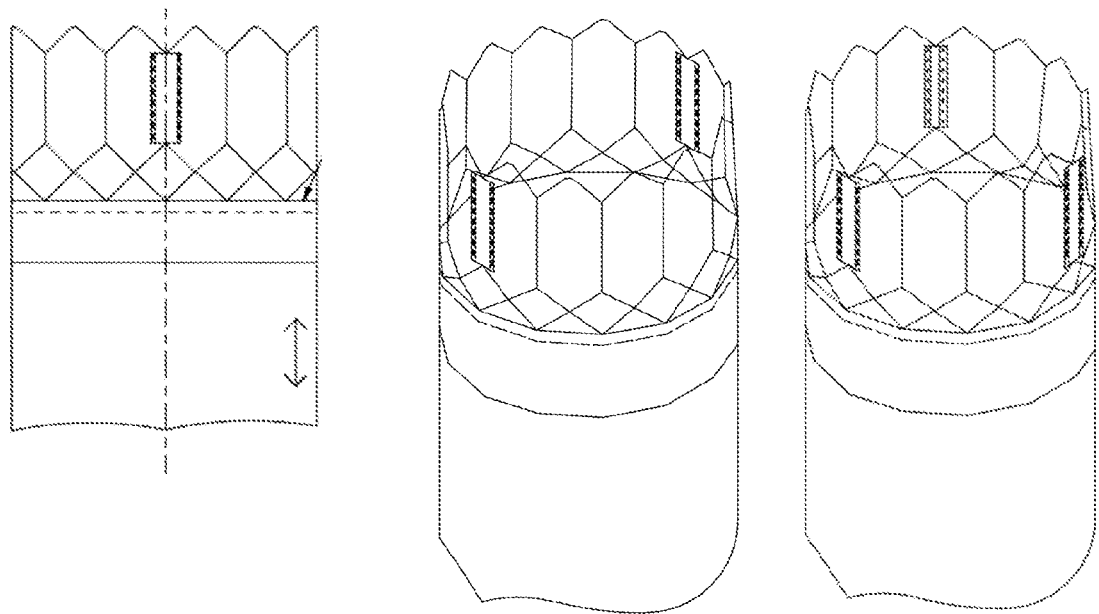
FIG. 1 shows the cuff sewn onto.

The invention relates to an innovative model of a polymer prosthetic heart valve, particularly aortic for transcatheter treatment of heart valve defects.

A low profile balloon expandable artificial prosthetic heart valve, particularly aortic, for transcatheter implantation comprises a cylindrical valve frame which consists of a valve section, a supporting section and a polymer material attached thereto. The polymer material in the form of one-piece cuff is inseparably integrated with the frame so that the valve frame in the supporting section is embedded and covered from the inside and from the outside with the cuff material. The cuff made of polymer material may also be attached, for example by sewing to the frame in the supporting section from the outside.

No matter how the cuff is attached, it is folded to the interior of the frame and in the frame valve section it is formed into valve leaflets in bicuspid or tricuspid configuration and in the said section it is attached to the frame and to the frame posts. The excess of the cuff material is led into the longitudinal openings in the posts and it is attached. Inseparably integrated with the frame cuff made of polymer material is favorably plaited by electrospinning. The cuff made of the polymer material, integrated with the frame is formed into the shape of the cylinder by hand. The valve leaflets are formed and attached to the posts by sewing, plaiting and/or by pressing, sewing and sticking in order to obtain a bicuspid or tricuspid configuration. The valve post is made in the form of longitudinal integral element of the valve frame and favorably along the longitudinal axis there is a longitudinal opening, and on the both sides of the said opening in the post circular openings are made. In the variant the post along the longitudinal axis has a longitudinal opening made, and the additional openings in the upper and lower sections are circular, and in the middle section they are oval. In another variant the post is made in the form of a longitudinal integral element of the valve frame and favorably along the longitudinal axis there is a longitudinal opening. In the variant favorably along the longitudinal axe of the post there are longitudinal openings. The polymer material which is used for forming the cuff and for forming the valve leaflets is folded into the frame interior and it is pulled through the opening or openings in the post, and the excess of the material is pressed to the post surface. In the valve variants the material excess is favorably sewn, pressed or sticked to the post.

The prosthetic heart valve of the present invention is characterized by high biocompatibility and of a low profile, which enables applying the delivery system of the smallest diameter possible. It adheres well to the aortic annulus in the supporting section for eliminating the risk of leakages. It is possible to reposition the valve with use of a special implantation system.

Use of the said methods for connecting the material and forming the valve leaflets enables coherence and ensures undisturbed valve activity with full coaptation (apposition) of the leaflets, which translates into a beneficial hemodynamic profile of the said prosthetic valve. Additionally, such methods improve mechanical properties and durability of the said prosthetic valve.

Furthermore, the method of forming the prosthetic heart valve and its leaflets considerably shortens the time of manufacturing which should significantly lower the production cost and increase the competitiveness of the product. It should translate into the widest possible use and further development of minimally invasive methods of repairing the aortic valve and other valves.

The invention relates to the prosthetic aortic valve comprising a metal stent (cobalt-chrome) of cylindrical design and a cuff covering the stent made of a polymer (artificial) material. Two applied methods of connecting allow to form a prosthetic aortic valve in bicuspid or tricuspid configuration.

Figure 2:
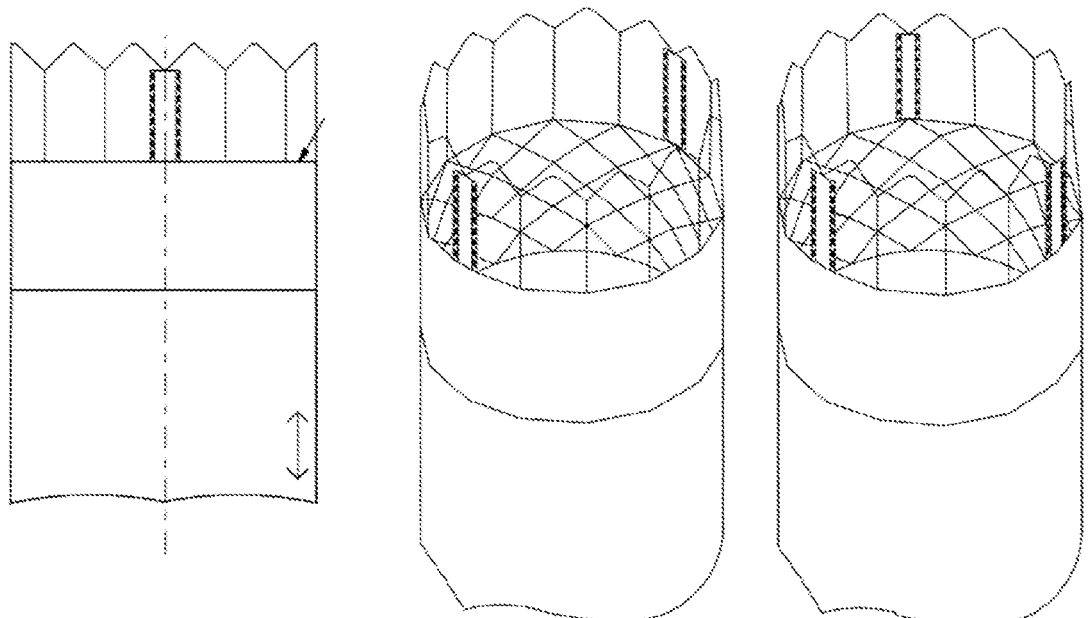
FIG. 2 shows the cuff plaited on the valve frame, with the view of two or three posts.
Figure 3:
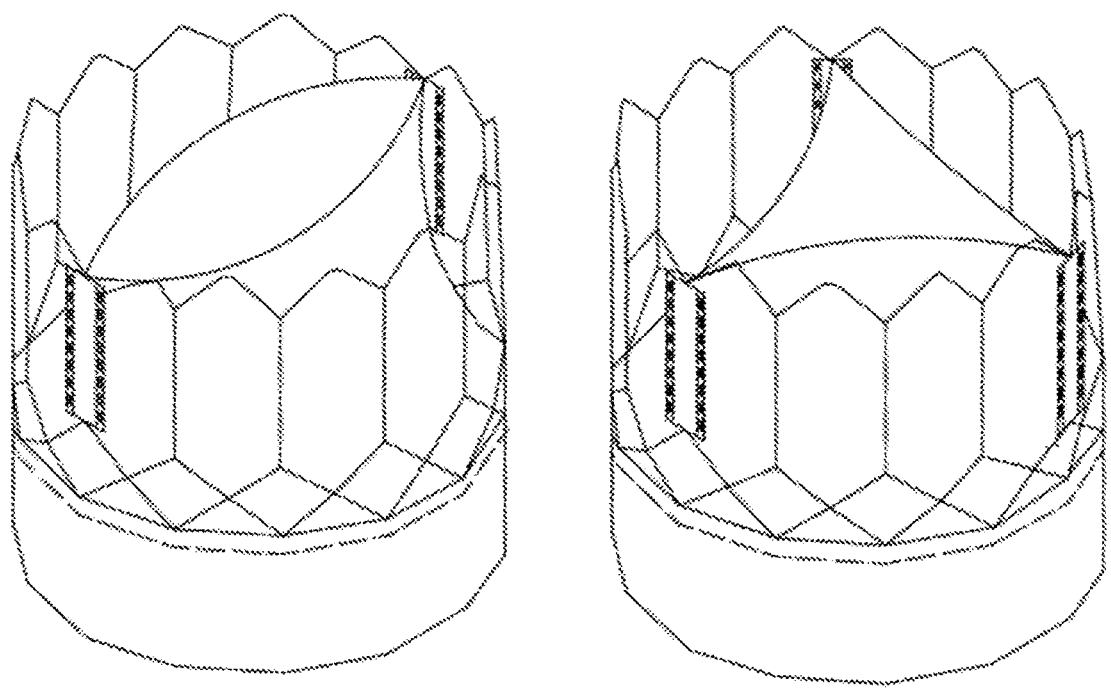
FIG. 3 shows the cuff stitched with formed valve leaflets in the bicuspid and tricuspid configurations.
Figure 4A:
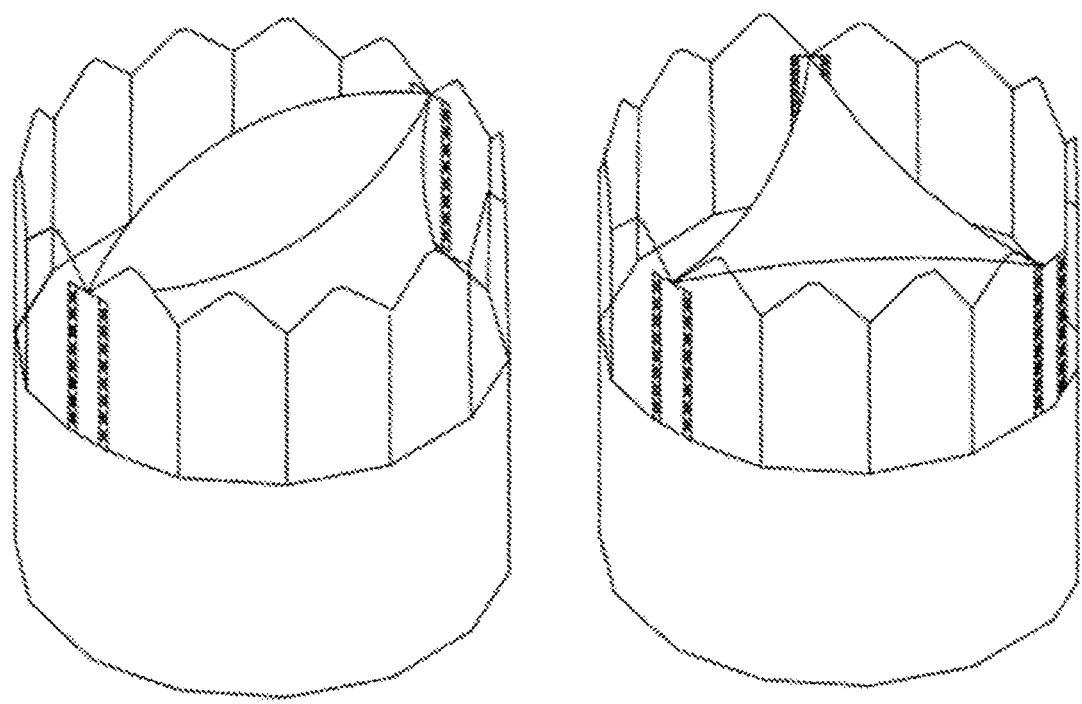
FIG. 4A shows a similar view for the cuff plaited on the frame.
Figure 4B:
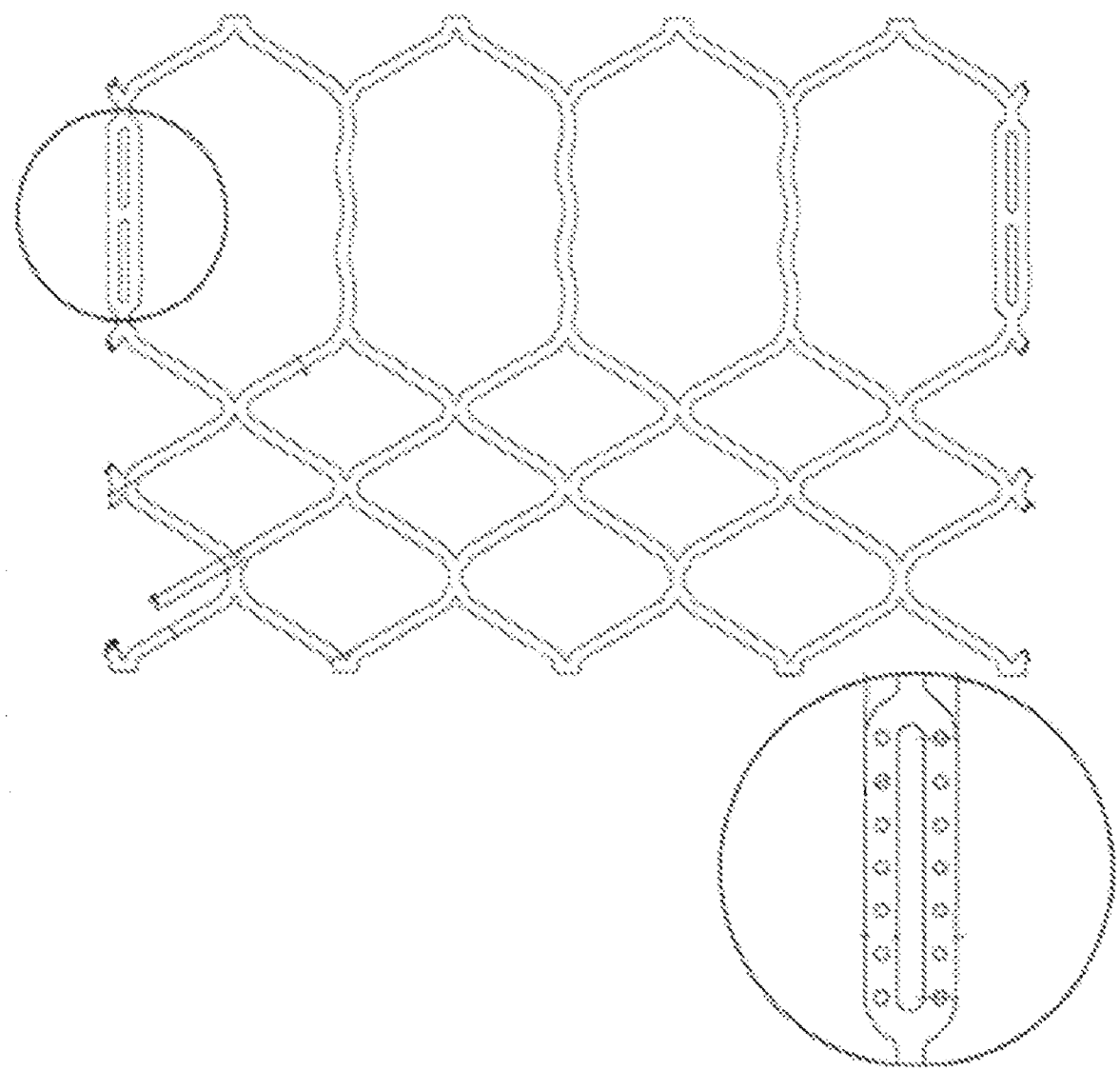
FIG. 4B shows the frame with the location of the posts.
Figure 6:
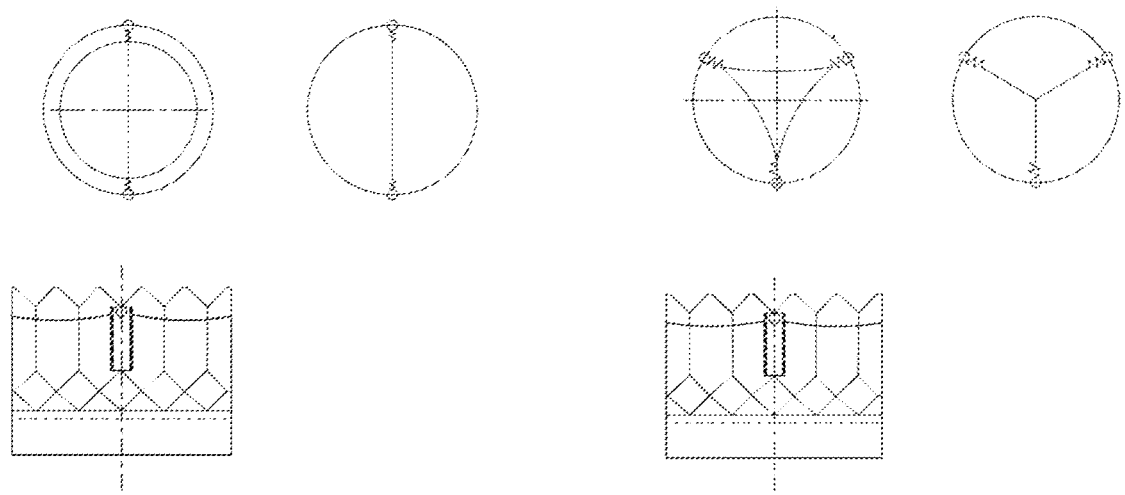
FIG. 6 shows two and three valve leaflets connected with the commissures in the open and closed position, with the cuff stitched.
Figure 7:
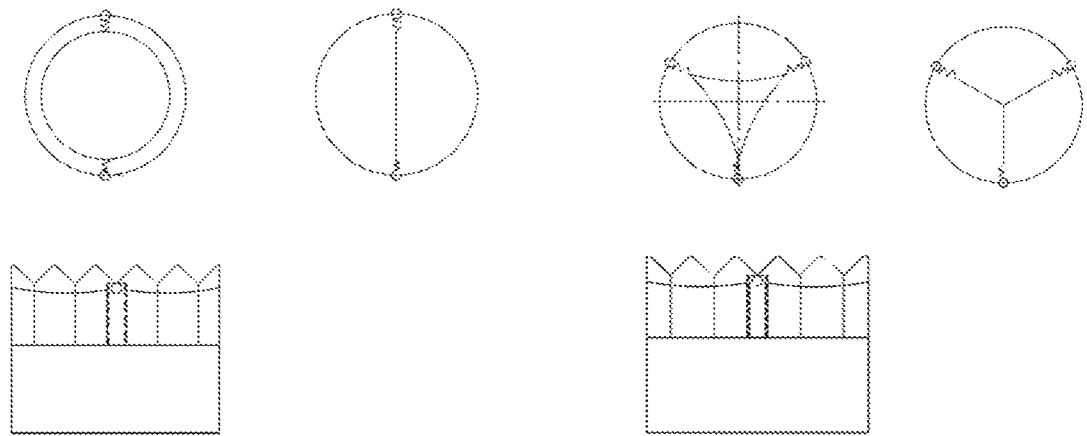
FIG. 7 similarly shows the valves with the cuff plaited.

The metal (cobalt-chrome) valve frame sized 16-29 mm of cylindrical design with the possibility for radial expansion comprising two sections:

The lower section (supporting) made of the posts 0.4 mm thick which are connected with each other in the manner ensuring durability and enabling plaiting the covering cuff with use of electrospinning, electro pollinating techniques or by sewing it onto the valve frame (FIGS. 1,2). The posts of the supporting section are connected with each other in a right-handed or left-handed design. The size of the basal meshes of the supporting section is in the range of 4-5 mm while the meshes of the middle section and the section connected with the valve frame are sized 3-4 mm.

The upper part (valve) consists of the posts located parallel to the axis of the supporting frame. The valve frame is made of two kinds of basal posts and the posts onto which the material is attached in order to form the valve leaflets.

The first (lower) ends of the valve frame posts are connected with the supporting frame struts while the others (upper) being connected to each other create the upper border of the valve.

Six different configurations of the posts are presented. FIG. 5 shows under letter A a longitudinal oval element inside which along the long axis there is a longitudinal opening of the diameter from 0.8 to 2 mm and of the length of 2 to 8 mm. In both outer edges of the opening there are 7 openings for plaiting the suture with the diameter in the range of 0.2-0.6 mm.

FIG. 5 under letter B shows a longitudinal oval element inside which along the long axis there is a longitudinal opening of the diameter from 0.8 to 2 mm and of the length of 2 to 8 mm. In both outer edges of the opening there are 4 openings, and 1 opening on each side of the inner opening in the upper and lower section has the shape of a circle with the diameter of 0.2 mm and the other openings in the middle section on both sides have the shape of a rectangle with rounded apexes of the length in the range of 1-2 mm and the diameter of 0.2-0.6 mm.

FIG. 5 under letter C shows A a longitudinal oval element inside which along the long axis there is a longitudinal opening of the diameter from 0.8 to 2 mm, the edges of the opening are smooth.

FIG. 5 under letter D shows a longitudinal oval element inside which along the long axis there are two openings in the whole long axis with the shape of a rectangle with rounded apexes where each opening has the diameter from 0.8-2 mm and the length of 0.8 to 2.5 mm.

FIG. 5 under letter E shows a longitudinal oval element inside which along the long axis there are three openings in the whole long axis with the shape of a rectangle with rounded apexes where each opening has the diameter from 0.8-2 mm and the length of 0.8 to 1.5 mm.

FIG. 5 under letter F shows a longitudinal oval element inside which along the long axis there are four openings in the whole long axis with the shape of a rectangle with rounded apexes where each slot has the diameter from 0.8-2 mm and the length of 0.8 to 1 mm.

Described above interstice openings for attaching the leaflets are located in the thickened longitudinal posts (in various variants) in the stent valve section, in which there are very small round openings for pulling and mounting the suture and atraumatic surgical needle.

The height of the valve frame mesh (in the direction parallel to the frame axis) is between 17 and 18 mm, branching off they connect with the adjacent struts of the valve frame also in a right-handed or left-handed design.

The design of the valve frame ensures fixed length of the frame in the process of compression and expansion. Additionally, it allows obtaining a low profile and coherent structure similar to a tube after tightening the stent.

Thanks to the post thickness change in the lower section and thanks to application of appropriate parameters the effect of "dog bone" is obtained in the scaffolding. The frame structure ensures low traumatization of tissues during implantation and thanks to high radial strength enables obtaining optimal hemodynamic parameters.

Example of the Connection No 1:

The cuff made of the polymer material plaited onto the inside and outside lower valve frame section constitutes the integral part of the invention. It is placed onto the stent by the method of electrospinning or electro pollening. The cuff covers the valve stent only partially (in the lower section) and it protrudes outside the stent borders, which produces the material excess in the form of a roll (one-part cuff) from which the valve leaflets are formed in the stent area by folding its free part to the inside section of the stent. Attaching the leaflets in this variant is by pulling the cuff material through the openings intended for this which are located in the valve section, from the inside to the outside of the frame (FIG. 5 items A,B,C) and pressing it.

Example of the Connection No 2:

The second variant of mounting consists of folding the free part of the cuff plaited onto the stent to inward the stent. The difference between this method and method no 1 is to create commissures of the leaflets from the polymer cuff by attaching them to dedicated openings (FIG. 5 items A,B,C, D,E,F) in the valve section of the frame with the surgical sutures.

Example of the Connection No 3:

The third variant of mounting consists of creating the commissures of the leaflets from the cuff both by pulling the folded in half material through the special longitudinal interstices in the stent located in the valve section of the valve (FIG. 5 items A,B,C) and attaching them to dedicated openings in the places of attaching in the frame with use of surgical sutures.

Example of the Connection No 4:

The fourth variant of mounting consists of creating the commissures of the leaflets from the cuff both by pulling the folded in half material through the special longitudinal interstices of the valve frame (FIG. 5 items A,B,C) and sticking them to the frame attaching element with the glue.

Example of the Connection No 5:

The material cuff (roll) formed from the polymer (artificial) material is afterwards partially sewn into the stent base. The free section of the stent is folded into the interior part of the stent and it is attached to the upper section of the frame so that it enables creating two or three symmetrical commissures. The material in the places of commissures is connected with the frame as it is described above in all the methods.

In all methods of connecting described above the cuff folded into the interior of the frame, in the section comprising the attaching elements, creates the valve leaflets of bicuspid or tricuspid configuration. At least one specification heading is required.

The invention claimed is:

1. A low profile balloon expandable artificial prosthetic heart valve, adapted for transcatheter implantation comprising:
   a valve frame of cylindrical structure which consists of a first section, a supporting section, defining a frame interior; and
   a single piece of continuous polymer material attached to the valve frame by electrospinning wherein an excess of the continuous polymer material forms a cuff of the polymer material which is inseparably integrated with the valve frame so that the valve frame supporting section is embedded and covered from inside of the valve frame and further covers an outside of the frame with the cuff material; further, a portion of the cuff is folded into the frame the frame interior and in the frame first section, it the cuff is formed into a valve leaflets in bicuspid or tricuspid configuration and in the said supporting section the continuous polymer is attached to the frame and to frame posts, each frame post having a central opening and longitudinal openings, an excess of the cuff material is pressed into the longitudinal openings in at least one of the posts to secure the cuff to the frame.

2. The low profile balloon expandable artificial prosthetic heart valve of claim 1 wherein the cuff is inseparably integrated with the frame made of a polymer material is plaited by an electrospinning method.

3. The low profile balloon expandable artificial prosthetic heart valve of claim 1 wherein the cuff made of the polymer material, integrated with the frame is formed into a shape of a cylinder by hand.

4. The low profile balloon expandable artificial prosthetic heart valve of claim 1 wherein the polymer material is bent inside the frame and the polymer material forms an inner cylinder whose end is folded into a shape mimicking valve leaflets by an attachment method comprising one of sewing, plaiting or by pressing, sewing and sticking in order to obtain a bicuspid or tricuspid configuration.

5. The low profile balloon expandable artificial prosthetic heart valve of claim 1 wherein the post is made in the form of longitudinal integral element of the valve frame and said central opening comprises a longitudinal slot and said longitudinal openings comprise circular slots.

6. The low profile balloon expandable artificial prosthetic heart valve of claim 1 wherein that the post is made in the form of a longitudinal integral element of the valve frame and along a longitudinal axis there is a longitudinal opening, and on both sides of the said opening in the post there are openings made, and the openings on the sides of the said openings in upper and lower sections are circular, and in middle section they are oval.

7. The low profile balloon expandable artificial prosthetic heart valve of claim 1 wherein the post is made in the form of a longitudinal integral element of the valve frame and said central opening comprises a longitudinal opening along the prosthetic aortic valve's longitudinal axis.

8. The low profile balloon expandable artificial prosthetic heart valve of claim 1 wherein the post is made in the form of a longitudinal integral element of the valve frame and the longitudinal openings along the longitudinal axis comprise circular longitudinal openings.

9. The low profile balloon expandable artificial prosthetic heart valve of claim 1 wherein the polymer material which is used for forming the cuff and for forming the valve leaflets is folded into the frame interior and it is pulled through the opening or openings in the post, and the excess of the material is pressed on top of the post's surface.

10. The low profile balloon expandable artificial prosthetic heart valve of claim 1 wherein the polymer material which is used for forming the cuff and for forming the valve leaflets is folded into the frame interior and it is pulled through the opening or slots in the post, and the excess of the material is sewn into the post.

11. The low profile balloon expandable artificial prosthetic heart valve of claim 1 wherein the polymer material which is used for forming the cuff and for forming the valve leaflets is folded into the frame interior and it is pulled through the opening in the post, and the excess of the material is pressed to the post.

12. The low profile balloon expandable artificial prosthetic heart valve of claim 1 wherein the polymer material which is used for forming the cuff and for forming the valve leaflets is folded into the frame interior and it is pulled through the opening in the post, and the excess of the material is stuck to the post.

13. The low profile balloon expandable artificial prosthetic heart valve of claim 1 wherein said frame comprises a metal stent of a cylindrical design.

14. The low profile balloon expandable artificial prosthetic heart valve of claim 1 wherein said frame posts have two sections with different configurations in each section, in a first section posts are parallel to the axis of the frame and a second section extensions from the posts are connected to each other to create an upper border.

15. The low profile balloon expandable artificial prosthetic heart valve of claim 14 wherein the folded over material is attached to posts comprising the second section.

16. The low profile balloon expandable artificial prosthetic heart valve of claim 14 wherein the cuff is placed onto the stent using electrospinning.

17. The low profile balloon expandable artificial prosthetic heart valve of claim 1 wherein the cuff covers the frame partially.

18. The low profile balloon expandable artificial prosthetic heart valve of claim 1 wherein the heart valve is an aortic valve.

* * * * *